US008730566B2

(12) United States Patent
Shuman

(10) Patent No.: US 8,730,566 B2
(45) Date of Patent: May 20, 2014

(54) GRATING BASED OPTICAL PARAMETRIC OSCILLATOR AND METHOD OF DYNAMICALLY TUNING THE OSCILLATOR FOR GENERATING DESIRED OPTICAL SIGNALS

(75) Inventor: Timothy M. Shuman, Purcellville, VA (US)

(73) Assignee: Exelis Inc., McLean, VA (US)

( * ) Notice: Subject to any disclaimer, the term of this patent is extended or adjusted under 35 U.S.C. 154(b) by 0 days.

(21) Appl. No.: 13/050,589

(22) Filed: Mar. 17, 2011

(65) Prior Publication Data
US 2012/0236395 A1 Sep. 20, 2012

(51) Int. Cl.
 *G02F 1/35* (2006.01)
 *H01S 3/10* (2006.01)
(52) U.S. Cl.
 USPC ................................ 359/330; 372/20; 372/21
(58) Field of Classification Search
 None
 See application file for complete search history.

(56) References Cited

U.S. PATENT DOCUMENTS

| 5,657,119 | A | 8/1997 | Kawasaki et al. | |
| 6,044,094 | A * | 3/2000 | Govorkov | 372/21 |
| 6,246,707 | B1 | 6/2001 | Yin et al. | |
| 6,751,010 | B1 | 6/2004 | Richter | |
| 7,724,788 | B2 | 5/2010 | Richter | |
| 2009/0129413 | A1 | 5/2009 | Richter | |
| 2009/0245297 | A1 | 10/2009 | Richter | |
| 2010/0296153 | A1* | 11/2010 | Jungbluth et al. | 359/328 |
| 2011/0261438 | A1* | 10/2011 | Vodopyanov | 359/330 |

FOREIGN PATENT DOCUMENTS

| DE | 19611015 A1 | 1/1998 |
| JP | 04067131 A | 3/1992 |
| JP | 2000514248 A | 10/2000 |
| WO | 9802777 | 1/1998 |
| WO | 2004017111 | 2/2004 |

OTHER PUBLICATIONS

European Search Report, EP12158004, Jun. 22, 2012, 11 pages.
S. Das, "Narrow linewidth pulsed optical parametric oscillator", PRAMANA journal of physics, vol. 75, No. 5, Nov. 2010, pp. 827-835.
F. Ganikhanov, T. Caughey, K. L. Vodopyanov: Narrow-linewidth middle-infrared ZnGeP2 optical parametric oscillator. Optical Society of America B/vol. 18, No. 6, Jun. 2001, pp. 818-822.

(Continued)

*Primary Examiner* — Hemang Sanghavi
(74) *Attorney, Agent, or Firm* — Edell, Shapiro & Finnan, LLC

(57) ABSTRACT

According to an embodiment of the present invention, an optical parametric oscillator (OPO) (e.g., for a laser transmitting device) includes non-linear optical media, optical beam manipulating elements, and a narrow linewidth filter in the form of a rotatable grating. The grating enables rapid tuning of the oscillator to provide an output beam with a desired wavelength. A pump laser provides a pump laser beam, and the non-linear optical media convert the pump beam into light beams with a signal wavelength and an idler wavelength. The angular positions or orientations of the non-linear optical media relative to a longitudinal propagation axis of the optical parametric oscillator (OPO) are adjustable to effectively tune the resulting signal and idler wavelengths. An output coupler receives the resulting beams from the non-linear optical media, and emits beams with the desired wavelength (signal and/or idler wavelengths).

20 Claims, 2 Drawing Sheets

(56) References Cited

OTHER PUBLICATIONS

Figure 1:
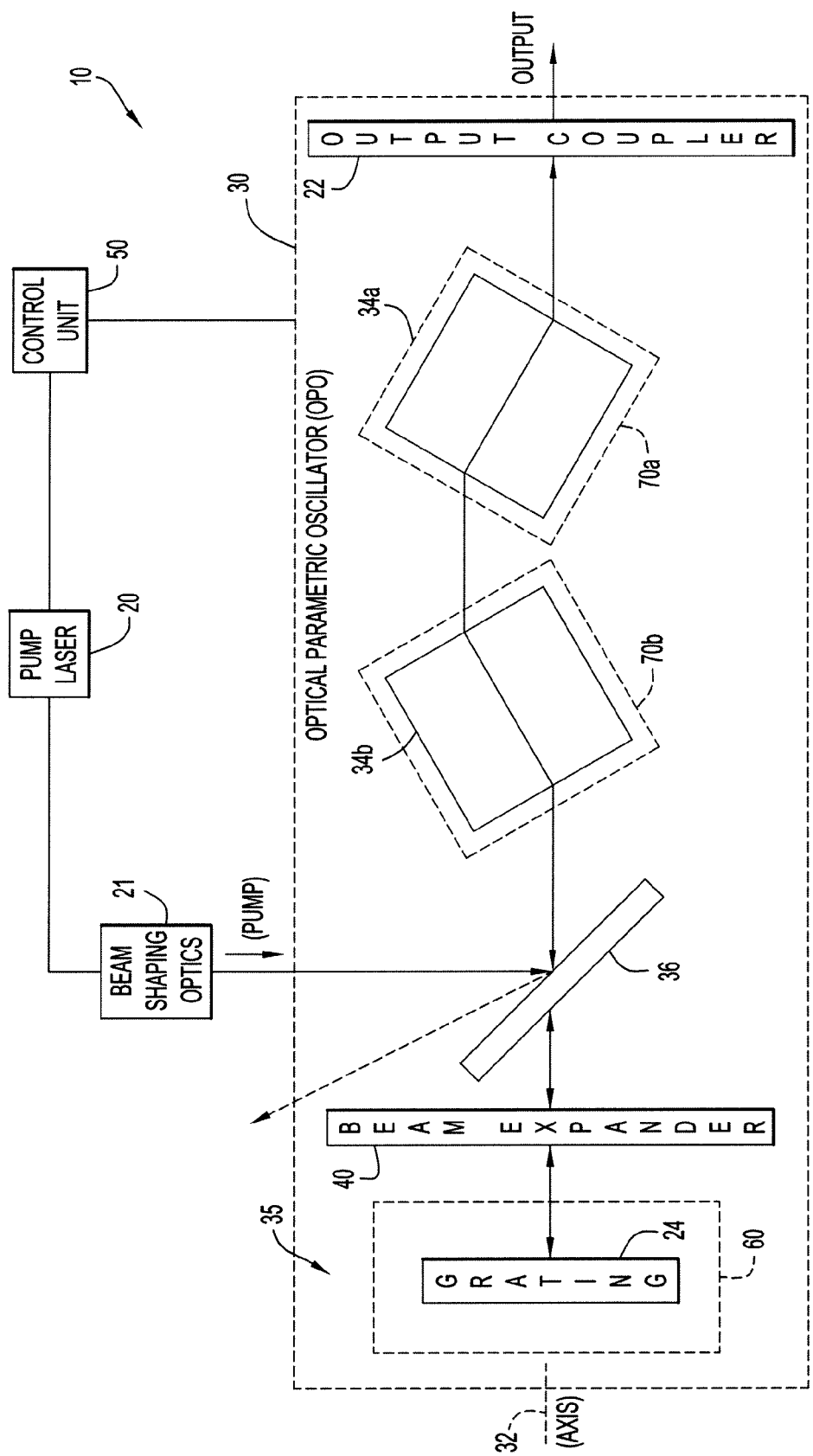

P. Weibring, J. N. Smith, H. Edner, S. Svanberg: Development and testing of a frequency-agile optical parametric oscillator system for differential absorption lidar. American Institute of Physics, vol. 74, No. 10, Oct. 2003, pp. 4478-4484.
European Search Report, Application No. 12 158 004.7-1904, Apr. 12, 2013, 8 pages.
Japanese Office Action and English Translation dated Jul. 31, 2013, 5 pages.
European Official Action dated Feb. 12, 2014, Application No. 12158004.7-1904, 12 pages.
Brosnan et al.: "Optical parametric oscillator threshold and linewidth studies", IEEE Journal of Quantum Electronics, vol. 15, No. 6, Jun. 1, 1979, pp. 415-431, XP055029808, ISSN: 0018-9197, DOI: 10.1109/JQE.1979.1070027.
Michael et al.: "New cavity design for a LiNbO3 optical parametric oscillator", Review of Scientific Instruments, vol. 57, No. 6, Jan. 1, 1986, p. 1210, XP055090291, ISSN: 0034-6748, DOI: 10.1063/1.1138632.
Minton et al.: "A scanning, single mode, LiNbO3, optical parametric oscillator", Optics Communications, North-Holland Publishing Co., Amsterdam, NL, vol. 69, No. 3-4, Jan. 1, 1989, pp. 289-293, XP024506541, ISSN: 0030-4018, DOI: 10.1016/0030-4018(89)90118-1.
"Motorized Zoom Beam Expander", Jan. 1, 2008, pp. 1-1, XP055091056, Retrieved from the Internet: URL: http://web.archive.org/web/20100724043900/http://specialoptics.com/products/beam_exp_motorized.html, retrieved on Dec. 2, 2013.

\* cited by examiner

GRATING BASED OPTICAL PARAMETRIC OSCILLATOR AND METHOD OF DYNAMICALLY TUNING THE OSCILLATOR FOR GENERATING DESIRED OPTICAL SIGNALS

BACKGROUND

1. Technical Field

The present invention embodiments pertain to devices producing optical signals. In particular, present invention embodiments pertain to an optical parametric oscillator (OPO) providing a narrow linewidth (e.g., optical spectrum width or band) over a tunable wavelength range and enhanced power output. The optical parametric oscillator (OPO) may be employed for detection of chemicals (e.g., narrow-line and broad feature (or wider-line)) and/or biological aerosols.

2. Discussion of Related Art

Optical parametric oscillators (OPO) are well-known, non-linear optical devices capable of producing coherent radiation at a desired frequency via parametric amplification. In a conventional optical parametric oscillator (OPO), a pump source supplies a beam of laser light at a pump wavelength to an optical cavity bounded by end mirrors and containing a non-linear optical medium (typically a non-linear optical crystal). As the pump beam propagates through the non-linear optical medium within the optical cavity, photons at the pump wavelength are converted into photon pairs at two longer wavelengths, thereby resulting in two lower-energy beams with these two longer wavelengths (conventionally referred to as the signal wavelength and the idler wavelength). The sum of the frequencies of the signal and idler beams (having the respective signal and idler wavelengths) equals the frequency of the pump beam. The particular wavelengths of the signal and idler beams are determined by a number of factors, including: the pump wavelength, the type and cut of the non-linear optical crystal, and the design of the optical cavity. In addition, tuning of the signal and idler beams can be achieved by adjusting the angle of the non-linear optical crystal.

Since typical operating conditions cause only a small fraction of the pump beam to be converted to the signal and idler beams in the initial pass through the non-linear optical crystal, the optical cavity of the optical parametric oscillator (OPO) is generally designed to oscillate one or both of the parametrically generated beams such that the signal and/or idler beam is amplified in successive passes through the non-linear optical crystal. The optical parametric oscillator (OPO) is considered a doubly resonant oscillator when both of the generated optical beams are resonated, and is considered a singly resonant oscillator when only one of the generated optical beams is resonated. Specifically, the optical cavity can be designed with end mirrors that reflect only one of the signal and idler frequencies (singly resonant), or with end mirrors that reflect both the signal and idler frequencies (doubly resonant).

An application of an optical parametric oscillator (OPO) is a light source for detection and/or identification of chemical/biological entities. With respect to remote sensing in the mid-wavelength infrared (MWIR) region, a wide variety of chemicals of interest have unique absorption features. One approach to sensing capitalizes on this characteristic by using a widely tunable (i.e., 3.1-3.6 microns) light source for both Differential Absorption Lidar (DIAL) and Differential Scattering (DISC) applications. However, the large tuning range of the light source prevents the optical parametric oscillator (OPO) from achieving linewidths (e.g., optical spectrum width or band) significantly lower than 300 picometers (pm), which is similar to the width of many narrow-line chemicals of interest (e.g., Hydrogen Chloride (HCl), etc.). Further, these narrow linewidths are not conducive for optimum measurements since an extremely tight tolerance is mandated on the central wavelength.

The above described oscillator functions adequately for chemicals with broad features requiring a broader linewidth (e.g., optical spectrum width or band) (e.g., dimethyl methylphosphonate (DMMP), triethyl phosphate (TEP), etc.). In order to provide the wide tuning range and the capability of measuring chemicals with either broad or narrow absorption features, a common solution employs a dual leg system. A first leg of the system contains an optical parametric oscillator (OPO) to perform measurements of chemicals with broad features, while the second leg of the system contains a narrow linewidth optical parametric amplifier (OPA) to measure the narrow-line chemicals. However, this system is impractical for the measurement of arbitrary chemicals. In particular, the optical parametric amplifier (OPA) requires seed lasers to generate the narrow linewidth, where the seed laser wavelengths are different for each chemical. Since a system to accommodate several chemicals requires a large number of these seed lasers, this type of system is extremely difficult to construct and expensive.

SUMMARY

According to an embodiment of the present invention, an optical parametric oscillator (OPO) (e.g., for a laser transmitting device) includes a cavity with a plurality of optical components including non-linear optical media, optical beam manipulating elements, and a narrow linewidth filter in the form of a rotatable grating. The grating enables rapid tuning of the oscillator to provide an output beam with a desired wavelength. A pump laser provides a pump laser beam with a pump wavelength to the cavity, and the non-linear optical media convert the pump beam into light beams with a signal wavelength and an idler wavelength that are each longer than the pump wavelength. The signal and/or idler wavelengths serve as the desired wavelength for the output beams. The angular positions or orientations of the non-linear optical media relative to a longitudinal propagation axis of the optical parametric oscillator (OPO) are adjustable to effectively tune the resulting signal and idler wavelengths. A beam shaping optical element converts the pump beam from the pump laser to a form compatible with the non-linear optical media prior to the pump beam entering the cavity. An output coupler receives the resulting beams from the non-linear optical media, and enables beams with the desired wavelength (signal and/or idler wavelengths) to be emitted from the cavity. Beams with other wavelengths are reflected back through the non-linear optical media and effectively resonate within the cavity.

A beam expander receives the beams reflected back through the non-linear optical media, and provides an expanded beam to the grating. The grating receives the expanded beam, and provides from the beam expander a resulting beam with a desired narrow linewidth for traversal through the non-linear optical media to emit a beam from the output coupler with the desired wavelength. Thus, beams within the cavity resonate therein to produce output beams with the desired wavelength. A galvanometer is provided for the grating and non-linear optical media to rotate these elements relative to the longitudinal propagation axis of the optical parametric oscillator (OPO) in order to adjust the wavelength of the output beam.

Present invention embodiments provide several advantages. For example, the grating dispersion tunes the wavelength of resonance (as the grating is rotated) within the cavity and maintains a narrow linewidth (e.g., optical spectrum width or band) over the tuning range. This enables the optical parametric oscillator (OPO) to perform measurements for narrow-line chemicals and chemicals with broad features (e.g., requiring a wider linewidth). For example, the grating enables the optical parametric oscillator (OPO) to provide a linewidth below 300 picometers (pm), and preferably on the order of 100 picometers (pm), with an upper limit for the linewidth on the order of several nanometers. Further, calibration of the grating requires measurement of only a few points, where the results are applied to a dispersion curve of the grating. This enables deterministic, dynamic (or "on-the-fly") tuning, and is advantageous when deploying a system in the field. In other words, since each angular orientation of the grating corresponds to a unique wavelength, deterministic and predictable tuning may be attained from sporadic calibration, and can be automated into an instrument for a self-check.

Further, the optical parametric oscillator (OPO) can be easily modified by changing the parameters of the beam expander used with the grating to meet the linewidth requirements of a wide variety of different applications. Moreover, the deterministic tuning enables a suitable control system to automatically calibrate and deliver customized sets of wavelengths for different applications, or alter the set of wavelengths during an application. Thus, the optical parametric oscillator (OPO) may provide varying tunable ranges depending upon an application. For example, the optical parametric oscillator (OPO) may provide tunable ranges of approximately 3-4 microns (e.g., with the idler wavelength beam serving as the output beams), and approximately 1.8-2.6 microns (e.g., with the idler and signal wavelength beams serving as the output beams).

In addition, alternative crystal materials (e.g., periodically poled lithium niobate (PPLN), rubidium titanyl arsenate (RTA), potassium titanyl arsenate (KTA), and the like each with a thickness in the approximate range of two to four millimeters) are preferably employed within the optical parametric oscillator (OPO) to attain an output power level on the order of watts. The upgrade in the power level significantly increases the distance range of the optical parametric oscillator (OPO) to render the system more capable in field test events (e.g., ranges on the order of kilometers). Moreover, the increased energy and ability to be dynamically tuned enables the optical parametric oscillator (OPO) to be employed for the investigation of biological aerosols.

The above and still further features and advantages of the present invention embodiments will become apparent upon consideration of the following detailed description of example embodiments thereof, particularly when taken in conjunction with the accompanying drawings wherein like reference numerals in the various figures are utilized to designate like components.

BRIEF DESCRIPTION OF THE DRAWINGS

FIG. 1 is a diagrammatic illustration of an optical parametric oscillator (OPO) according to an embodiment of the present invention employed in an example laser transmitting device.

FIG. 2 is a procedural flowchart illustrating the manner in which the optical parametric oscillator (OPO) produces a desired beam according to an embodiment of the present invention.

DETAILED DESCRIPTION OF EXAMPLE EMBODIMENTS

Present invention embodiments pertain to an optical parametric oscillator (OPO) providing a narrow linewidth (e.g., optical spectrum width or band) over a tunable wavelength range and enhanced power output. This enables the optical parametric oscillator (OPO) to be employed for detection of various chemicals (e.g., narrow-line and broad feature (or wider-line)) and/or biological aerosols. The optical parametric oscillator (OPO) includes a rotatable grating that enables rapid tuning of the oscillator. Since each angular orientation of the grating corresponds to a unique wavelength, deterministic and predictable tuning may be attained from sporadic calibration, and can be automated to provide customized sets of wavelengths for different applications, or alter the set of wavelengths during an application. In addition, alternative crystal materials (e.g., periodically poled lithium niobate (PPLN), rubidium titanyl arsenate (RTA), potassium titanyl arsenate (KTA), and the like each with a thickness in the approximate range of two to four millimeters) are preferably employed within the optical parametric oscillator (OPO) to attain an increased output power level. The increased power level and the ability to be dynamically tuned enables the optical parametric oscillator (OPO) to be employed for the investigation of biological aerosols.

An optical parametric oscillator (OPO) according to an embodiment of the present invention employed within an example laser transmitting device is illustrated in FIG. 1. In particular, laser transmitting device 10 includes a pump laser 20, beam shaping optics 21, an optical parametric oscillator (OPO) 30, and a control unit 50. Pump laser 20 provides an initial laser beam to enable optical parametric oscillator (OPO) 30 to produce an output beam at a desired wavelength as described below. The pump laser may be implemented by any conventional or other laser transmitting device providing an appropriate laser beam (e.g., an SLM Nd:YAG pump laser having up to a 2 kHz repetition rate or any other laser device with a relatively narrow linewidth, etc.). Beam shaping optics 21 receives an emitted laser beam from pump laser 20, and shapes the received beam to produce a beam compatible with non-linear optical media of optical parametric oscillator (OPO) 30. The beam produced by beam shaping optics 21 is provided to optical parametric oscillator (OPO) 30 to generate an output beam with a desired wavelength as described below. Beam shaping optics 21 may include any quantity of any conventional or other optical devices (e.g., lenses, mirrors, reflectors, refractors, prisms, etc.) to produce a beam compatible with optical parametric oscillator (OPO) 30.

Optical parametric oscillator (OPO) 30 basically performs wavelength conversion to mid-wavelength infrared (MWIR) laser lines, and provides rapid tuning between different wavelengths. This enables the optical parametric oscillator (OPO) to be employed for detection and identification of chemical (e.g., narrow-line and broad feature) and biological substances. For example, chemical or biological substances with narrow spectral linewidths require laser linewidths of approximately 10% of the substance absorption features for accurate measurements, while substances with broad features (or wider linewidths) require multiple laser lines and spectral linewidths consistent with atmospheric transmission windows. The parametric optical oscillator (OPO) accommodates both narrow-line and broad feature substances.

Optical parametric oscillator (OPO) 30 includes an output coupler 22, a grating 24, non-linear optical media including a pair of non-linear optical crystals 34*a*, 34*b*, a pump mirror 36, and a beam expander 40, each disposed within a cavity 35.

The cavity is preferably enclosed to maintain the beams therein. Grating 24 is mounted or otherwise secured to a corresponding rotating assembly 60, while non-linear optical crystals 34a, 34b are each similarly mounted or otherwise secured to respective rotating assemblies 70a, 70b. The rotating assemblies may be implemented by any conventional or other devices to rotate, or alter the angular orientation of, the grating and non-linear optical media (e.g., galvanometer, etc.). Grating 24 and non-linear optical crystals 34a, 34b are rotatable via rotating assemblies 60, 70a, 70b to adjust an angle of orientation of those components relative to a longitudinal propagation axis 32 of optical parametric oscillator (OPO) 30. The orientation of the grating primarily controls the wavelength, where the linewidth (e.g., optical spectrum width or band) of the beam varies with the wavelength. The density of the grooves or slots of the grating and the size of the beam produced by the beam expander define the resulting linewidth. The orientation of the non-linear optical crystals controls the wavelengths of the beam produced by the crystals as described below. Thus, the orientations of the grating and non-linear optical crystals are cooperatively controlled to emit a beam with the desired wavelength from optical parametric oscillator (OPO) 30. Control unit 50 controls pump laser 20, rotating assemblies 60, 70a, 70b, and the configuration of beam expander 40 to control generation of the beam emitted from optical parametric oscillator (OPO) 30 as described below.

Non-linear optical crystals 34a, 34b are disposed between output coupler 22 and pump mirror 36. Pump mirror 36 is preferably implemented by a dichroic mirror, but any conventional or other reflective device or surface (e.g., mirror, lens, prism, etc.) may be utilized. Since the pump mirror has a high reflectivity (HR) property for beams with the pump wavelength, pump mirror 36 directs the pump beam from beam shaping optics 21 to non-linear optical crystals 34a, 34b.

As the pump beam propagates through non-linear optical crystals 34a, 34b, photons at the pump wavelength are converted into photon pairs at two longer wavelengths, thereby resulting in two beams with these two longer wavelengths (referred to as the signal wavelength and the idler wavelength). Accordingly, the beam with the pump wavelength from pump mirror 36 is converted by non-linear optical crystals 34a, 34b to beams with the signal and idler wavelengths. The angular position or orientation of each of the non-linear optical crystals relative to longitudinal propagation axis 32 is controlled by control unit 50 (via rotating assemblies 70a, 70b) to control apportionment of magnitude at the signal and idler wavelengths as described below. This embodiment of optical parametric oscillator (OPO) 30 is described with respect to producing an output beam with an idler wavelength serving as the desired wavelength. However, optical parametric oscillator (OPO) 30 may be configured in other embodiments to produce output beams with other desired wavelengths (e.g., signal wavelength, signal and idler wavelengths, etc.) as described below.

Non-linear optical crystals 34a, 34b may be implemented by any suitable materials (e.g., periodically poled lithium niobate (PPLN), rubidium titanyl arsenate (RTA), potassium titanyl arsenate (KTA), etc.), any derivations thereof, or any combinations of the foregoing. The non-linear optical crystals preferably have a thickness in the approximate range of two to four millimeters (2-4 mm) in order to increase the power to a level on the order of watts. The upgrade in the power level significantly increases the distance range for utilization of the optical parametric oscillator (OPO) (e.g., ranges on the order of kilometers). However, the non-linear optical crystals may alternatively be implemented by any suitable optical medium of any desired size, shape, or thickness (e.g., linear, non-linear, crystals or other material forms, etc.) that produces the desired optical signals and power levels.

Different materials and/or different crystal lengths for non-linear optical crystals 34a, 34b may be employed within optical parametric oscillator (OPO) 30 to accommodate varying application requirements (e.g., where non-linear optical crystals 34a, 34b may include the same or different materials with the same or different thicknesses and/or crystal lengths). Varying these characteristics can enable modification of linewidths without the use of beam expander 40. This technique may further be applied for generating different wavelengths simultaneously within optical parametric oscillator (OPO) 30 (with different conversion efficiencies). Moreover, different crystal properties may be utilized to maximize conversion for a single wavelength, or a plurality of wavelengths.

Output coupler 22 is coupled to non-linear optical crystal 34a and provides the output beam emitted from optical parametric oscillator (OPO) 30. The output coupler may be implemented by any conventional or other devices filtering optical signals (e.g., an opticoupler, etc.). Output coupler 22 has a high reflectivity (HR) property for beams with the pump and signal wavelengths, and a high transmissivity (HT) property for beams with the idler wavelength. Accordingly, the output coupler serves to pass a beam with a desired (idler) wavelength, and reflect beams with other wavelengths (signal and pump wavelengths) back through the non-linear optical crystals to pump mirror 36 as described below. This traversal of beams with pump and signal wavelengths back through non-linear optical crystals 34a, 34b generates additional gain for the idler wavelength.

Beam expander 40 is coupled to pump mirror 36. Since pump mirror 36 has a high transmissivity (HT) property for beams with the idler wavelength, the beams with the idler wavelength received from non-linear optical crystals 34a, 34b are passed by the pump mirror to the beam expander. The pump mirror further has a transmissivity property for beams with the signal wavelength to remove these beams (reflected by output coupler 22) from optical parametric oscillator (OPO) 30. Beam expander 40 receives beams (with idler wavelengths) from pump mirror 36, and expands those beams onto grating 24. The beam expander may be implemented by any conventional or other optical devices expanding and/or compressing optical signals.

Grating 24 is coupled to beam expander 40, and receives the expanded beams from the beam expander. The grating may be implemented by any conventional or other devices dispersing optical signals (e.g., grating, materials with slits/slots, etc.), and may include any desired configuration (e.g., any quantity and arrangement of slits/slots, etc.) to produce desired optical signals. The dispersion of the grating tunes the wavelength of resonance (as the grating is rotated) within cavity 35, and maintains a narrow linewidth (e.g., optical spectrum width or band) over the tuning range. In other words, each angular orientation of grating 24 corresponds to a unique wavelength, thereby enabling deterministic and predictable tuning. The grating enables optical parametric oscillator (OPO) 30 to perform measurements for narrow-line chemicals and chemicals with broad features (e.g., requiring a wider linewidth). For example, the grating enables the optical parametric oscillator (OPO) to provide a linewidth below 300 picometers (pm), and preferably on the order of 100 picometers (pm), with an upper limit for the linewidth on the order of several nanometers.

Conventional optical parametric oscillators (OPO) typically employ an etalon to filter beams and produce the linewidth. However, the etalon is difficult to use since etalons typically cannot tune widely without generating multiple free spectral ranges (or tuning bands). Further, a time-consuming manual calibration is required for the etalon that cannot be automated easily and must be performed routinely.

In contrast, calibration of grating 24 within optical parametric oscillator (OPO) 30 of a present invention embodiment requires measurement of only a few points, where the results are applied to a dispersion curve of the grating. Since each angular orientation of grating 24 corresponds to a unique wavelength as discussed above, deterministic and predictable tuning may be automated and attained from sporadic calibration. The deterministic tuning enables a suitable control system (e.g., control unit 50) to automatically calibrate and deliver customized sets of wavelengths for different applications, or alter the set of wavelengths during an application. In addition, optical parametric oscillator (OPO) 30 can be easily modified by changing (e.g., via control unit 50) the parameters of beam expander 40 used with grating 24 to meet the linewidth requirements of a wide variety of different applications (e.g., for detection of narrow-line or broad feature chemicals, biological entities, etc.). Thus, the optical parametric oscillator (OPO) may provide varying tunable ranges depending upon an application. For example, the optical parametric oscillator (OPO) may provide tunable ranges of approximately 3-4 microns (e.g., with the idler wavelength beam serving as the output beams), and approximately 1.8-2.6 microns (e.g., with the idler and signal wavelength beams serving as the output beams).

Grating 24 provides to beam expander 40 a beam with the desired wavelength (idler wavelength) based on the grating orientation relative to longitudinal propagation axis 32. The beam expander returns the beam from the grating back to the dimensions prior to expansion for transference to pump mirror 36. Since the pump mirror has a high transmissivity (HT) property for beams with the idler wavelength and a high reflectivity (HR) property for beams with the pump wavelength as described above, the beam from the beam expander is passed to the non-linear optical crystals along with the beam from pump laser 20 to produce the output beam with the desired (idler) wavelength.

Control unit 50 controls the operation of pump laser 20, rotatable assemblies 60, 70a, 70b, and the configuration of beam expander 40 to enable optical parametric oscillator (OPO) 30 to produce the output beam with the desired wavelength. The control unit may implemented by any conventional or other computing or processing device (e.g., personal or other computer system, controller, microprocessor, circuitry, etc.), and is configured with suitable parameters (and/or software and/or hardware modules) to control pump laser 20, rotatable assemblies 60, 70a, 70b, and beam expander 40 to achieve the desired tuned wavelength output, repetition rate, and rapid scanning across the tunable range of optical parametric oscillator (OPO) 30 (e.g., real-time scanning, where wavelength characteristics may be changed on the order of one-thousand times per second and the tunable range may be scanned in less than three seconds).

In particular, control unit 50 configures beam expander 40 and controls rotating assemblies 60, 70a, 70b to control the angular position or orientation of grating 24 and non-linear optical crystals 34a, 34b relative to longitudinal propagation axis 32. The angular position or orientation of grating 24 and configuration of beam expander 40 control the linewidth (e.g., optical spectrum width or band), while the angular position or orientation of non-linear optical crystals 34a, 34b controls the magnitude apportioned to the signal and idler wavelengths. Thus, the angular positions or orientations of the grating and non-linear optical crystals are cooperatively controlled to produce the desired beam within optical parametric oscillator (OPO) 30. The parameters may be provided (or entered) by a user (for control unit 50) to configure the laser transmitting device to produce a desired output beam.

Once the parameters are provided, the beam expander is configured and the grating and non-linear optical crystals are rotated to appropriate angular positions or orientations, pump laser 20 supplies laser beam pulses with the pump wavelength to optical parametric oscillator (OPO) 30. Non-linear optical crystals 34a, 34b convert the laser beam pulses at the pump wavelength to beams at the signal wavelength and idler wavelength, and output coupler 22 provides the desired output beam. Optical parametric oscillator (OPO) 30 may be configured to provide output beams with the idler wavelength, the signal wavelength, or any combination thereof.

Figure 2:
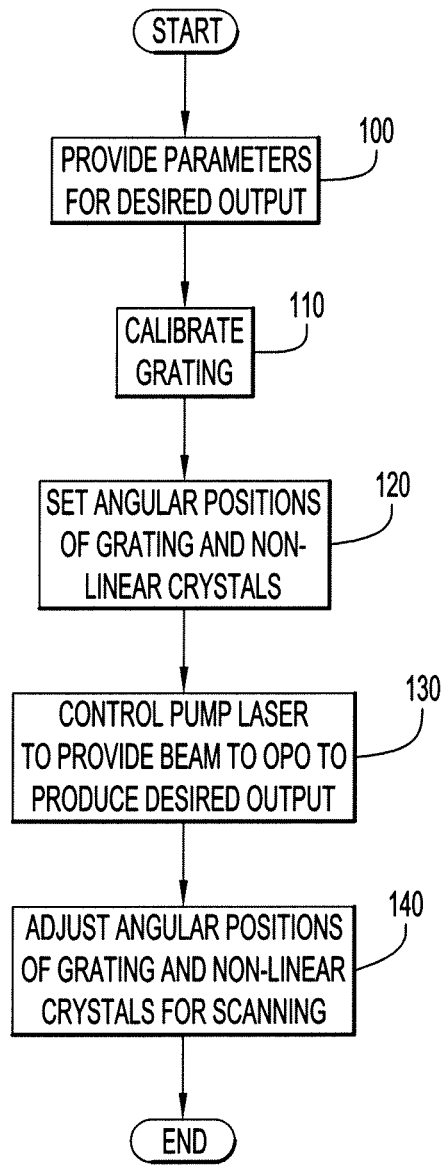

A manner of producing an output beam with a desired wavelength from optical parametric oscillator 30 is illustrated in FIG. 2. Initially, a user provides parameters to control unit 50 to produce an output beam with a desired wavelength at step 100, and the control unit calibrates grating 24 for operation at step 110. The control unit measures a few points for the calibration (e.g., via a sensor not shown), and applies the measurement results to a dispersion curve of the grating. The dispersion curve is utilized for determining the appropriate angular position of the grating for tuning. The calibration may be performed at any time interval.

Control unit 50 further configures beam expander 40 and controls rotating assemblies 60, 70a, 70b in accordance with the provided parameters to initially set the angular positions for grating 24 and non-linear optical crystals 34a, 34b to produce the desired output beam at step 120. Pump laser 20 is controlled to provide a beam with the pump wavelength to optical parametric oscillator (OPO) 30 to generate the desired output beam at step 130. In particular, pump laser 20 directs a beam through beam shaping optics 21 that converts the beam to a form compatible with non-linear optical crystals 34a, 34b. The converted beam with the pump wavelength is reflected from pump mirror 36 through non-linear optical crystals 34a, 34b to generate beams with the signal and idler wavelengths. The angular positions or orientations of the non-linear optical crystals control the amount of magnitude apportioned to each wavelength, where the ratio of energies at each wavelength is constant. The signal and idler wavelengths generated may be determined from the following expression.

$$1/\lambda_{PUMP} = 1/\lambda_{SIGNAL} + 1/\lambda_{IDLER},$$

where $\lambda_{PUMP}$ represents the pump wavelength, $\lambda_{SIGNAL}$ represents the signal wavelength, and $\lambda_{IDLER}$ represents the idler wavelength. For example, when the pump laser supplies a pump beam with a pump wavelength of 1.064 microns, and the non-linear optical crystals 34a, 34b are tuned to some arbitrary wavelength (e.g., 1.550 microns), the output beam of optical parametric oscillator (OPO) 30 at the idler wavelength is approximately 3.4 microns.

As the pump beam from pump laser 20 traverses non-linear optical crystals 34a, 34b from pump mirror 36, beams with the signal and idler wavelengths are generated and accumulate some gain. Output coupler 22 enables the generated beams with the idler wavelength to pass as the output beam, and reflects beams with the pump and signal wavelengths back through the non-linear optical crystals 34a, 34b to pump mirror 36. As the beams (with the signal and pump wavelengths) reflected from output coupler 22 traverse non-linear optical crystals 34a, 34b, the non-linear optical crystals continue to generate gain for the idler wavelength. Pump mirror 36 reflects the beams with the pump wavelength from the non-linear optical crystals back toward those crystals, while removing beams with the signal wavelength from the optical parametric oscillator (OPO). Thus, the beam with the pump wavelength continually passes in both directions through non-linear optical crystals 34a, 34b to generate beams with the signal and idler wavelengths as described above. Accordingly, beams with the signal wavelength partially resonate in optical parametric oscillator (OPO) 30 between output coupler 22 and pump mirror 36 prior to the pump mirror removing those beams.

Pump mirror 36 further receives beams with the idler wavelength from non-linear optical crystals 34a, 34b, and passes those beams to beam expander 40. The beam expander expands the beam onto grating 24, where the grating generates a beam with a desired wavelength based on the grating angular position as described above. The generated beam is compressed by beam expander 40 to dimensions prior to the expansion, and provided with the desired linewidth back to pump mirror 36. The beams pass through pump mirror 36 and non-linear optical crystals 34a, 34b to output coupler 22 that provides the beam as the output beam. Thus, each iteration of beams with the idler wavelength passing through grating 24 and beam expander 40 enable these components to further narrow the beam linewidth (e.g., optical spectrum width or band), thereby enabling the resonating beams to converge to the desired (idler) wavelength. Accordingly, beams with the idler wavelength partially resonate in optical parametric oscillator (OPO) 30 between output coupler 22 and grating 24 prior to the output coupler passing the beam with the idler wavelength as the output beam.

This embodiment of optical parametric oscillator (OPO) 30 pertains to the case where the idler wavelength serves as the desired wavelength. However, optical parametric oscillator (OPO) 30 may be configured for other embodiments to provide beams with any desired wavelengths (e.g., signal and/or idler wavelengths). This may be accomplished by adjusting the characteristics of pump mirror 36 and output coupler 22. These characteristics may be adjusted by utilizing different components with the desired characteristics, or additional optical components to manipulate the beams to a desired form. For example, in a case where a beam with the signal wavelength is desired, the characteristics of pump mirror 36 may be adjusted to remove beams with the idler wavelength, and pass beams with the signal wavelength (to the beam expander and grating). Similarly, the characteristics of output coupler 22 may be adjusted to pass beams with the signal wavelength (as the output beam), and reflect beams with the pump and idler wavelengths. The angular positions or orientations of the grating and non-linear optical crystals may further be adjusted to provide this desired output. The beams in this case traverse (and partially resonate within) the optical parametric oscillator (OPO) in a manner similar to the manner described above to generate the desired output beam with the signal wavelength. Thus, beams with the idler wavelength (generated during traversal of the non-linear optical crystals) partially resonate in optical parametric oscillator (OPO) 30 between output coupler 22 and pump mirror 36 prior to the pump mirror removing those beams, and beams with the signal wavelength (generated by the grating and during traversal of the non-linear optical crystals) partially resonate in optical parametric oscillator (OPO) 30 between output coupler 22 and grating 24 prior to the output coupler passing the beam with the signal wavelength as the output beam.

By way of further example, in a case where beams with the signal and idler wavelengths are desired, the characteristics of pump mirror 36 may be adjusted to reflect beams with signal and pump wavelengths, and pass beams with the idler wavelength (to the beam expander and grating). Similarly, the characteristics of output coupler 22 may be adjusted to pass beams with the signal and idler wavelengths (as the output beams), and reflect beams with the pump wavelength. The angular positions or orientations of the grating and non-linear optical crystals may further be adjusted to provide this desired output. The beams in this case traverse (and partially resonate within) the optical parametric oscillator (OPO) in a manner similar to the manner described above to generate the desired output beams with the signal and idler wavelengths. Thus, beams with the signal wavelength (generated during traversal of the non-linear optical crystals) partially resonate in optical parametric oscillator (OPO) 30 between output coupler 22 and pump mirror 36, while beams with the idler wavelength (generated by the grating and during traversal of the non-linear optical crystals) partially resonate in optical parametric oscillator (OPO) 30 between output coupler 22 and grating 24 prior to the output coupler passing the beams with the signal and idler wavelengths as the output beams.

Once the beam is produced at a desired wavelength within a tunable range for an appropriate time interval (e.g., sufficient to detect substances, etc.), the angular positions or orientations of grating 24 and non-linear optical crystals 34a, 34b are adjusted for the next desired wavelength in a scan at step 140. When grating 24 is adjusted to produce a beam with a new wavelength, the produced beam is injected into the resonating portions of cavity 35, where the resonances within the optical parametric oscillator (OPO) converge to that new wavelength. Control unit 50 awaits completion of the transition to the new wavelength within cavity 35 prior to enabling output from the optical parametric oscillator (OPO). This enables the wavelengths within the tunable range of the optical parametric oscillator (OPO) to be scanned.

A primary focus for mid-wavelength infrared (MWIR) development relates to the detection and identification of airborne chemicals. In this case, optical parametric oscillator (OPO) 30 may be configured to produce beams of various linewidths for detection of narrow-line and broad feature chemicals. However, since optical parametric oscillator (OPO) 30 provides increased energy levels and the ability to be dynamically tuned as described above, the optical parametric oscillator (OPO) is further suited for investigation of the frequency dependence of mid-wavelength infrared (MWIR) backscatter signals from biological aerosols. In other words, the optical parametric oscillator (OPO) of present invention embodiments may be utilized (e.g., in a Differential Scattering (DISC) technique) to identify aerosol components in the atmosphere, and provides significantly more information than existing aerosol backscatter systems. In this case, optical parametric oscillator (OPO) 30 is configured to produce beams of narrow linewidths (e.g., less than 300 picometers (pm), and preferably on the order of 100 picometers (pm)) suitable for detection of these biological aerosols. In addition, emitting in the mid-wavelength infrared (MWIR) region retains the potential of the device to remain eye-safe. Thus, optical parametric oscillator (OPO) 30 may be configured to produce beams of various linewidths (e.g., to accommodate both narrow-line and broad feature substances) for use in various applications.

It will be appreciated that the embodiments described above and illustrated in the drawings represent only a few of the many ways of implementing a grating based optical parametric oscillator and method of dynamically tuning the oscillator for generating desired optical signals.

The optical parametric oscillator (OPO) of present invention embodiments may be employed within any suitable devices to generate a desired signal (e.g., transmitting devices, receiving devices, transceiving devices, etc.), and may be utilized with signals of any desired energy (e.g., light, laser, signals of any frequency or wavelength, etc.). The optical parametric oscillator (OPO) may provide a tunable range of approximately 1.8-4 microns, and linewidths below 300 picometers (pm), preferably extending to linewidths on the order of approximately 100 picometers (pm). Thus, the optical parametric oscillator (OPO) may be configured to detect any narrow-lined and/or broad feature substances (e.g., chemicals, biological aerosols and/or other entities, etc.). The components of the optical parametric oscillator (OPO) may be arranged in any fashion to produce any desired beam flow therein and generate a desired signal. In addition, the optical parametric oscillator (OPO) may be configured to generate any desired signals based on the signal wavelength, idler wavelength, or any combination thereof.

The pump laser may be implemented by any quantity of any conventional or other laser transmitting device providing an appropriate laser beam (e.g., an SLM Nd:YAG pump laser having up to a 2 kHz repetition rate or any other laser device with a relatively narrow linewidth, etc.). The pump laser may be arranged to provide a signal into the optical parametric oscillator (OPO) at any desired location or point in the beam flow. The beam shaping optics may include any quantity of any conventional or other optical devices (e.g., lenses, mirrors, reflectors, refractors, prisms, etc.) to produce any desired beam or signal compatible with the optical parametric oscillator. The pump mirror may be implemented by any quantity of any conventional or other reflective devices or surfaces (e.g., mirror, lens, prism, etc.). The pump mirror may be configured in any desired manner to reflect and/or pass any desired signals. The output coupler may be implemented by any quantity of any conventional or other devices filtering optical signals (e.g., an opticoupler, etc.). The output coupler may be configured in any desired manner to reflect and/or pass any desired signals.

The non-linear optical medium may include any quantity of any suitable materials (e.g., periodically poled lithium niobate (PPLN), rubidium titanyl arsenate (RTA), potassium titanyl arsenate (KTA), etc.), any derivations thereof, or any combinations of the foregoing. The non-linear optical medium may be of any desired size, shape, or thickness (e.g., linear, non-linear, crystals or other material forms, etc.) that produces the desired optical signals and power levels. The non-linear optical crystals may include the same or different materials with the same or different thicknesses and/or crystal lengths. Varying the characteristics of the non-linear optical medium may enable modification of linewidths without the use of a beam expander.

The beam expander may be implemented by any quantity of any conventional or other optical devices expanding and/or compressing optical signals at any desirable expansion and/or compression ratios. The grating may be implemented by any quantity of any conventional or other devices dispersing optical signals (e.g., grating, materials with slits/slots, etc.), and may include any desired configuration (e.g., any quantity and arrangement of slits/slots, etc.) to produce desired optical signals. The grating may be configured such that each angular orientation of the grating may corresponds to any desired wavelength.

The rotating assemblies may be implemented by any conventional or other devices to rotate, or alter the angular orientation of, the grating and non-linear optical media (e.g., galvanometer, etc.). The rotating assemblies may be employed to rotate any other components of the optical parametric oscillator (OPO).

The control unit employed by present invention embodiments may be implemented by any quantity of any personal or other type of computer or processing device (e.g., IBM-compatible computer, APPLE, MACINTOSH, laptop, PDA, controller, microprocessor, etc.), and may include any commercially available operating system (e.g., Windows, OS/2, Unix, Linux, etc.) and any commercially available or custom software (e.g., control software, etc.). These devices may include any types of monitors and input devices (e.g., keyboard, mouse, voice recognition, touch screen, etc.) to enter and/or view information.

It is to be understood that any software for the control unit of present invention embodiments may be implemented in any desired computer language and could be developed by one of ordinary skill in the computer arts based on the functional descriptions contained in the specification and flow charts illustrated in the drawings. Further, any references herein of software performing various functions generally refer to computer systems or processors performing those functions under software control. The control unit of present invention embodiments may alternatively be implemented by any type of hardware and/or other processing circuitry. The various functions of the control unit may be distributed in any manner among any quantity of software modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). The software and/or processes described above and illustrated in the flow charts may be modified in any manner that accomplishes the functions described herein. In addition, the functions in the flow charts or description may be performed in any order that accomplishes a desired operation.

The software of present invention embodiments may be available on a program product apparatus or device including a recordable or computer usable medium (e.g., magnetic or optical mediums, magneto-optic mediums, floppy diskettes, CD-ROM, DVD, memory devices, etc.) for use on stand-alone systems or systems connected by a network or other communications medium, and/or may be downloaded (e.g., in the form of carrier waves, packets, etc.) to systems via a network or other communications medium.

Although described with respect to wavelengths, present invention embodiments may similarly be applied with respect to generation of signals with desired frequencies. The thickness of the non-linear optical medium is preferably in the approximate range of two to four millimeters to attain an output power level on the order of watts (e.g., greater than one watt), but may be of any thickness to provide desirable power levels.

It is to be understood that the terms "top", "bottom", "front", "rear", "side", "height", "length", "width", "upper", "lower", "vertical" and the like are used herein merely to describe points of reference and do not limit the present invention to any particular orientation or configuration. It is to be further understood that the terms "comprises", "comprising", "includes", "including", "has", "have", "having", "with" and the like, when used in this specification and the claims, specify the presence of stated features, but do not preclude the presence or addition of one or more other features.

From the foregoing description, it will be appreciated that the invention makes available a novel grating based optical parametric oscillator and method of dynamically tuning the oscillator for generating desired optical signals, wherein the optical parametric oscillator (OPO) provides a narrow linewidth (e.g., optical spectrum width or band) over a tunable wavelength range and enhanced power output.

Having described preferred embodiments of a new and improved grating based optical parametric oscillator and method of dynamically tuning the oscillator for generating desired optical signals, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. An apparatus to generate a desired optical signal comprising:
    an optical oscillator including:
        at least one optical medium to produce optical medium signals with first and second wavelengths in response to an optical signal with a third wavelength traversing said at least one optical medium, wherein said desired optical signal includes said second wavelength;
        a grating to produce a grating optical signal, wherein each angular orientation of said grating relative to a longitudinal axis of said optical oscillator produces said grating optical signal with a different wavelength range;
        an optical element disposed between said grating and said at least one optical medium to direct corresponding optical signals toward said grating and said at least one optical medium and to remove said optical medium signals with said first wavelength from said optical oscillator, wherein said corresponding optical signals include said grating optical signal and said optical medium signals;
        a beam expander coupled between said optical element and said grating to expand optical signals from said optical element on said grating and to compress optical signals received from said grating for said optical element;
        a coupler coupled to said at least one optical medium to emit said desired optical signal from said optical oscillator with a desired linewidth and said second wavelength;
    a plurality of rotating assemblies to rotate said grating and each said at least one optical medium to tune said optical oscillator to generate said desired optical signal; and
    a control unit to scan across a tunable range of said optical oscillator, wherein said control unit is configured to:
        receive user-specified parameters;
        dynamically tune said optical oscillator and produce said desired optical signal for a time interval by controlling a configuration of said beam expander and said rotating assemblies to control angular orientations of said grating and said at least one optical medium in accordance with said user-specified parameters, wherein said grating is controlled and calibrated in accordance with a dispersion curve; and
        adjust said rotating assemblies to adjust said angular orientations of said grating and said at least one optical medium after said time interval to produce said desired optical signal at a next desired wavelength in said scan and delay emission of said desired optical signal from said optical oscillator until optical signals from said adjusted angular orientations converge to said next desired wavelength.

2. The apparatus of claim 1, wherein said desired optical signal includes a laser signal.

3. The apparatus of claim 1, wherein said optical oscillator is tuned to produce said desired optical signal with a wavelength within a range of approximately 1.8-4 microns.

4. The apparatus of claim 1, wherein said desired linewidth is less than 300 picometers.

5. The apparatus of claim 4, wherein said desired linewidth is approximately 100 picometers.

6. The apparatus of claim 1, wherein a thickness of said at least one optical medium is in the approximate range of two to four millimeters to produce said desired optical signal with a power level greater than one watt.

7. The apparatus of claim 1, wherein said first wavelength includes a signal wavelength, said second wavelength includes an idler wavelength, and said coupler emits said desired optical signal including said idler wavelength.

8. The apparatus of claim 1, further comprising:
    a laser device to produce a laser signal; and
    optics to manipulate said laser signal to form a pump signal compatible with said optical oscillator, and to provide said pump signal to said optical element within said optical oscillator.

9. The apparatus of claim 1, wherein said desired linewidth enables detection of at least one of chemicals and biological entities.

10. The apparatus of claim 1, wherein said control unit calibrates said grating based on measurements of said grating optical signal and signal dispersion curve.

11. A method of generating a desired optical signal within an optical oscillator comprising:
    producing optical medium signals with first and second wavelengths via at least one rotatable optical medium in response to an optical signal with a third wavelength traversing said at least one optical medium, wherein said desired optical signal includes said second wavelength;
    generating a grating optical signal via a rotatable grating, wherein each angular orientation of said grating produces said grating optical signal with a different wavelength range;
    directing corresponding optical signals toward said grating and said at least one optical medium and removing optical medium signals with said first wavelength from said optical oscillator via an optical element, wherein said corresponding optical signals include said grating optical signal and said optical medium signals;
    expanding optical signals from said optical element on said gating and compressing optical signals received from said grating for said optical element via a beam expander;
    emitting said desired optical signal with a desired linewidth and a wavelength of said second wavelength via a coupler coupled to said at least one optical medium; and
    scanning across a tunable range of said optical oscillator, via a control unit, by dynamically tuning said grating and each said at least one optical medium to generate said desired optical signal by rotating said grating and each said at least one optical medium, wherein said scanning includes:
        receiving user-specified parameters;
        controlling a configuration of said beam expander and angular orientations of said grating and said at least one optical medium in accordance with said user-specified parameters to dynamically produce said desired optical signal for a time interval, wherein said grating is controlled and calibrated in accordance with a dispersion curve; and adjusting said angular orientations of said grating and said at least one optical medium after said time interval to produce said desired optical signal at a next desired wavelength in said scan and delaying emission of said desired optical signal from said optical oscillator until optical signals from said adjusted angular orientations converge to said next desired wavelength.

12. The method of claim 11, wherein said desired optical signal includes a laser signal.

13. The method of claim 11, wherein said tuning further includes:
tuning said grating and each said at least one optical medium to produce said desired optical signal with a wavelength within a range of approximately 1.8-4 microns.

14. The method of claim 11, wherein said desired linewidth is less than 300 picometers.

15. The method of claim 14, wherein said desired linewidth is approximately 100 picometers.

16. The method of claim 11, wherein a thickness of said at least one optical medium is in the approximate range of two to four millimeters to produce said desired optical signal with a power level greater than one watt.

17. The method of claim 11, wherein said first wavelength includes a signal wavelength, said second wavelength includes an idler wavelength, and said emitting further includes:
emitting said desired optical signal including a wavelength of said idler wavelength.

18. The method of claim 11, further comprising:
producing a laser signal via a laser device;
manipulating said laser signal via optics to form a pump signal compatible with said at least one optical medium; and
directing said pump signal from said optics to said optical element.

19. The method of claim 11, wherein said desired linewidth enables detection of at least one of chemicals and biological entities.

20. The method of claim 11, further including:
calibrating said grating based on measurements of said grating optical signal and said dispersion curve.

* * * * *